United States Patent [19]

Rasshofer

[11] Patent Number: 4,507,464

[45] Date of Patent: Mar. 26, 1985

[54] POLYISOCYANATES PREPARED BY PHOSGENATING A POLYAMINE IN THE PRESENCE OF A COMPOUND CONTAINING AT LEAST ONE HYDROXYL GROUP

[75] Inventor: Werner Rasshofer, Cologne, Fed. Rep. of Germany

[73] Assignee: Bayer Aktiengesellschaft, Leverkusen, Fed. Rep. of Germany

[21] Appl. No.: 578,911

[22] Filed: Feb. 10, 1984

[30] Foreign Application Priority Data

Feb. 26, 1983 [DE] Fed. Rep. of Germany ....... 3306845

[51] Int. Cl.³ .............................................. C08G 18/10
[52] U.S. Cl. .................................... 528/288; 525/439; 528/372; 560/25; 560/24; 560/157; 560/158; 560/159
[58] Field of Search ................. 528/288, 372; 525/439; 560/24, 25, 157, 158, 159

[56] References Cited

U.S. PATENT DOCUMENTS

| | | | |
|---|---|---|---|
| 3,251,803 | 5/1966 | Caldwell et al. | 528/372 |
| 3,835,172 | 9/1974 | Arndt et al. | 260/453 PH |
| 4,386,218 | 5/1983 | Rasshofer et al. | 564/38 |

OTHER PUBLICATIONS

High Polymers, vol. XVI "Polyurethanes", Part I, by J. H. Saunders and K. C. Frisch, Interscience Publishers (1962), p. 365.

Kunststoff–Handbuch, vol. VII, "Polyurethane" by R. Vieweg and A. Hochtlen, Carl-Hanser-Verlag, Munich (1966), pp. 447–451 and 758.

*Primary Examiner*—Maurice J. Welsh
*Attorney, Agent, or Firm*—Gene Harsh; Joseph C. Gil; Lyndanne M. Whalen

[57] ABSTRACT

Polyisocyanates are produced by phosgenating a primary polyamine in the presence of at least one compound containing at least one primary and/or secondary alcoholic hydroxyl group in accordance with techniques known in the art. The reactants are used in quantities such that the equivalent ratio of primary amino groups to alcoholic hydroxyl group of from 1:0.005 to 1:0.99 is maintained during the phosgenation reaction. Where phosgenation is carried out in a two-stage process, the compound containing alcoholic hydroxyl groups must at least be present in the required quantity during the second stage. The primary polyamine may optionally be converted into a phosgenatable salt or a carbon dioxide adduct prior to being phosgenated to form the polyisocyanate. The polyisocyanates thus-produced may then be used in the production of polyurethanes or polyamines.

20 Claims, No Drawings

POLYISOCYANATES PREPARED BY PHOSGENATING A POLYAMINE IN THE PRESENCE OF A COMPOUND CONTAINING AT LEAST ONE HYDROXYL GROUP

BACKGROUND OF THE INVENTION

This invention relates to a new process for the production of polyisocyanates. The present invention also relates to the compounds obtainable by this process and to their use in the production of polyurethane plastics or production of the corresponding polyamines.

In the production of polyurethane plastics from polyisocyanates and polyhydroxyl compounds, the so-called prepolymer or semiprepolymer process is an important alternative. In this process, a prepolymer containing free isocyanate groups or a semiprepolymer (a mixture of prepolymer with excess monomeric starting polyisocyanate) is prepared in a first stage from excess polyisocyanate and the polyhydroxyl component. In a second stage, the prepolymer is reacted with a chain-extending agent to form a high molecular weight polyurethane (cf. for example High Polymers, Vol. XVI "Polyurethanes", Part I, by J. H. Saunders and K. C. Frisch, Interscience Publishers (1962), or Kunststoff-Handbuch, Vol. VII, "Polyurethane" by R. Vieweg and A. Hochtlen, Carl Hanser Verlag, Munich (1966)).

One disadvantage of this known process is that production of the NCO-prepolymers or NCO-semiprepolymers requires a separate reaction step in which some of the NCO-groups in the starting polyisocyanate are reacted with the alcoholic hydroxyl groups of the hydroxyl component.

SUMMARY OF THE INVENTION

It is an object of the present invention to provide a simpler process for the production of NCO-prepolymers or NCO-semiprepolymers. It is another object of the present invention to provide a process in which the distillation residue obtained in the commercial production of distillable polyisocyanates (such as for example tolylene diisocyanate or hexamethylene diisocyanate) accumulates in a liquid consistency such that the polyisocyanate may be used for further reactions.

These and other objects which will be apparent to those skilled in the art are achieved by phosgenating primary amines in the presence of the polyhydroxyl compounds generally incorporated through urethane groups in NCO-prepolymers or NCO-semiprepolymers. The corresponding NCO-prepolymers or NCO-semiprepolymers are thereby obtained directly in a single reaction step. Phosgenation of primary polyamines using substoichiometric quantities of monohydric and polyhydric alcohols by the process of the present invention produces distillable polyisocyanates of which the distillation residues (in contrast to the distillation residues obtained in the working up of diisocyanato-toluene by distillation) accumulate in a more fluid and more readily processible consistency.

DETAILED DESCRIPTION OF THE INVENTION

The present invention relates to a process for the production of polyisocyanates in which primary polyamines (optionally after they have been converted into phosgenatable salts or carbon dioxide adducts by known methods) are phosgenated in one or two stages. During the phosgenation and/or at least in the second stage of a two-stage phosgenation process, at least one compound containing at least one primary and/or secondary alcoholic hydroxyl group should be present in a quantity such that the equivalent ratio of primary amino groups present in the starting amine to hydroxyl groups of from 1:0.005 to 1:0.99 is maintained during the reaction. The present invention also relates to polyisocyanates obtainable by this process.

The present invention also relates to the use of the polyisocyanates obtainable by the above-described process as a synthesis component in the production of polyurethane plastics by the isocyanate polyaddition process. These polyisocyanates may also be used as a starting material for the production of the corresponding polyamines by the hydrolytic conversion of their isocyanate groups into amino groups.

In addition to saving one process step, the process of the present invention has a number of other advantages over known two-stage processes for the production of NCO-prepolymers. For example, in the process of the present invention, it is not necessary to use free monomeric polyisocyanates so that the need for safety measures with respect to such monomeric materials is eliminated. In the process of the present invention, NCO-prepolymers substantially free from monomers are produced simply by selecting an appropriate equivalent ratio between amino groups and hydroxyl groups (for example in the range from 1:0.5 to 1:0.99) without the need to remove (e.g., by thin-layer distillation) unreacted starting isocyanates. In addition, the process of the present invention is suitable for the production of NCO-prepolymers based on any polyisocyanates whereas, in the old two-stage process, it was often imperative to use only diisocyanates having isocyanate groups of differing reactivity.

The polyamines which may be used as starting materials in the process of the present invention are any organic compounds which contain at least two primary amino groups, but are otherwise inert under the reaction conditions, and which have a molecular weight in the range from 60 to 500 (preferably from 108 to 250). Aromatic polyamines having a molecular weight within these ranges are particularly preferred starting materials.

Examples of suitable aromatic diamines include: 2,4-diaminotoluene; 2,6-diaminotoluene; 1,4-diaminobenzene; 2,4-diaminomesitylene; 1,3,5-triethyl-2,4-diaminobenzene; 1,3,5-triisopropyl-2,4-diaminobenzene; 1-methyl-3,5-diethyl-2,4-diaminobenzene; 1-methyl-3,5-diethyl-2,6-diaminobenzene; 4,6-dimethyl-2-ethyl-1,3-diaminobenzene; 1,5-diaminonaphthalene; 1,8-diaminonaphthalene; 2,7-diaminonaphthalene; 4,4'-diaminodiphenylmethane; 2,4'-diaminodiphenylmethane; 2,2'-diaminodiphenylmethane; 3,3'-dimethyl-4,4'-diaminodiphenylmethane; 4-methyl-3,4'-diaminodiphenylmethane; 3,5,3',5'-tetraethyl-4,4-diaminodiphenylmethane; 3,5,3',5'-tetraisopropyl-4,4'-diaminodiphenylmethane; 3,5-diethyl-3',5'-diisopropyl-4,4'-diaminodiphenylmethane; 2,2-bis-(4-aminophenyl)-propane; 1,1-bis-(4-aminophenyl)-cyclohexane; 1,1-bis-(4-amino-3-methylphenyl)-cyclohexane; 3,5- and 2,4-diaminobenzoic acid esters according to German Offenlegungsschrift 20 25 900; diamines containing ester groups according to German Offenlegungsschriften 18 03 635, 20 40 650 and 21 60 589; diamines containing ether groups according to German Offenlegungsschriften 17 70 525 and 18 09 172 (U.S. Pat. Nos.

3,654,364 and 3,736,295); 2-halogen-1,3-phenylene diamines optionally substituted in the 5-position (German Offenlegungsschriften 20 01 772, 20 25 896 and 20 65 869); 3,3'-dichloro-4,4'-diaminodiphenylmethane; 4,4'-diaminodiphenylsulfides according to German Offenlegungsschrift 24 04 976; diaminodiphenylthioethers according to German Offenlegungsschrift 25 09 404; aromatic diamines substituted by alkylthio groups according to German Offenlegungsschrift 26 38 760; diaminobenzene phosphoric acid esters according to German Offenlegungsschrift 24 59 491; aromatic diamines containing sulfonate or carboxylate groups according to German Offenlegungsschrift 27 20 166; the high-melting diamines disclosed in German Offenlegungsschrift 26 35 400; aminoalkylthioanilines according to German Offenlegungsschrift 27 34 574 (aromatic-aliphatic diamines); and mixtures of these polyamines.

It is less preferred to use aliphatic polyamines such as, for example, linear or branched aliphatic diamines. Specific examples of such polyamines are: 1,2-diaminoethane; 1,6-diaminohexane; 2,2,4-trimethyl-1,6-diaminohexane; 1,8-diamino-octane; 1,5-diamino-3-oxapentane; 1,8-diamino-3,6-dioxaoctane; 1,11-diamino-3,6,9-trioxaundecane. Cycloaliphatic diamines, such as 5-amino-2,2,4-trimethyl-1-cyclopentanemethylamine; 5-amino-2-aminomethyl-1,3,3-trimethylcyclohexane; 1,4-diaminocyclohexane; 1,3-diaminocyclohexane; 1,8-diamino-p-methane; 1-methyl-2,6-diaminocyclohexane; 1-methyl-2,4-diaminocyclohexane; 4,4'-diaminodicyclohexylmethane and its 2,4'- and 2,2'-isomers; 4,4'-diamino-3,3'-dimethyldicyclohexylmethane and its 2,4'- and 2,2'-isomers; 4,4'-diaminodicyclohexylethane; 4,4'-diaminodicyclohexylether; bis-(4-aminocyclohexyl)-2,2-propane; 4,4'-diamino-dicyclohexane; 4,4'-diamino-3,3'-diethyldicyclohexylmethane; 1,1-di-(4'-aminocyclohexyl)-cyclohexane; 1,1-di-(4'-amino-3'-methylcyclohexyl)-cyclohexane; 4,4'-diamino-3,5-diethyl-3',5'-diisopropyl-dicyclohexylmethane; 4,4'-diamino-3,3',5,5'-tetraethyl-dicyclohexylmethane; and mixtures thereof are also less preferred.

In the practical application of the process of the present invention, the polyamines mentioned by way of example are used in admixture with at least one organic compound which contains at least one primary and/or secondary alcoholic hydroxyl group. This compound containing alcoholic hydroxyl group(s) is otherwise inert under the conditions of the process of the present invention. The compound containing alcoholic hydroxyl group(s) has a molecular weight in the range from 32 to 10,000. This alcoholic component preferably has an (average) hydroxyl functionality of from 2 to 3 and an (average) molecular weight of from 62 to 6000 (preferably from 400 to 3000). Specific examples of suitable alcohols are:

(a) alkane polyols free from ether and ester groups, especially those having a molecular weight in the range from 62 to 250, such as ethylene glycol; 1,2-propane diol; 1,3-propane diol; 1,2-, 1,3-, 2,3-, 1,4-butane diol; 1,5-pentane diol; neopentyl glycol; 1,6-hexane diol; 2,5-dimethyl-2,5-hexane diol; 2,2,4-trimethyl-1,3-pentane diol; trimethyl-1,6-hexane diols; 1,12-octadecane diol; trimethylol propane; glycerol; trimethylol ethane; hexane triols; sorbitol; mannitol and pentaerythritol;

(b) cycloalkane polyols free from ether and ester groups, especially those having a molecular weight in the range from 116 to 250, such as 1,2-, 1,3- and 1,4-dihydroxycyclohexane; 2,2,4,4-tetramethyl-1,3-cyclobutane diol; 1,4-cyclohexane dimethanol; 4,4'-dihydroxy dicyclohexylmethane and 2,2-bis-(4-hydroxycyclohexyl)-propane;

(c) polyols containing ether groups, especially those having a molecular weight in the range from 106 to 10,000, such as diethylene glycol; triethylene glycol; tetraethylene glycol; dipropylene glycol; tripropylene glycol; tetrapropylene glycol or the polyether polyols known to those skilled in polyurethane chemistry having molecular weights in the above-mentioned ranges which may be obtained in known manner by alkoxylating suitable starter molecules, such as the compounds mentioned in (a) and (b), using ethylene oxide and/or propylene oxide;

(d) polyols containing ester groups, especially those having a molecular weight in the range from 206 to 10,000, such as succinic acid-bis-(2-hydroxyethyl)ester; adipic acid-bis-(2-hydroxyethyl)-ester; and in particular, the relatively high molecular weight polyester polyols known in polyurethane chemistry having molecular weights in the above-mentioned ranges, of the type obtained in known manner by reacting polyhydric alcohols of the type mentioned above (in particular in a), with substoichiometric quantities of dicarboxylic acids or dicarboxylic acid anhydrides (such as, for example, adipic acid, phthalic acid, phthalic acid anhydride, tetrahydrophthalic acid or tetrahydrophthalic acid anhydride); and (e) mixtures of the alcohols mentioned in (a) through (d).

Alcohols containing at least two hydroxyl groups are preferably used as the alcohol component. However, it is also possible in principle to use monohydric alcohols having a molecular weight in the range from 32 to approximately 250, such as methanol, ethanol, 1-propanol, 2-propanol, 1-butanol, 1-hexanol, 1-decanol, 1-octadecanol, 2-methoxyethanol, cyclohexanol, 2-phenylethanol, 1-phenoxy-2-propanol and mixtures of monohydric alcohols such as these as the sole alcoholic component or in combination with polyhydric alcohols.

Other suitable, although less preferred alcohols are alcohols containing heteroatoms, such as aminopolyether polyols of the type obtained by alkoxylating compounds containing amino groups (such as ammonia, aniline, phenylene diamines, ethanolamine or propanolamine); polythioethers, particularly the condensation products of thiodiglycol on its own and/or with other glycols, dicarboxylic acids, formaldehyde, aminocarboxylic acids or aminoalcohols; polyacetals such as the compounds obtainable from glycols (such as diethylene glycol or triethylene glycol) and formaldehyde; or polycarbonates containing hydroxyl groups such as those which may be obtained by reacting diols with diphenylcarbonate or phosgene.

Further examples of suitable alcohols for hydroxyl compounds may be found, for example, in High Polymers, Vol. XVI, "Polyurethanes, Chemistry and Technology", by Saunders-Frisch, Interscience Publishers, New York/London, Vol. I, 1962, pages 32 to 42 and pages 44 to 54 and Vol. II, 1964, pages 5–6 and 198–199, and also in Kunststoff-Handbuch, Vol. VII, Vieweg-Hochtlen, Carl-Hanser-Verlag, Munich, 1966, for example on pages 45 to 71.

In the practical application of the process of the present invention, the compounds containing hydroxyl groups are used in a quantity such that for every primary amino group present in the polyamine to be phosgenated there are from 0.005 to 0.99, preferably from 0.1 to 0.8 and, most preferably, from 0.1 to 0.6 alcoholic hydroxyl groups.

The process of the present invention is carried out in a manner analogous to known processes for the phosgenation of primary amines. Examples of such phosgenation processes are described for example by S. Petersen in Houben-Weyl/Muller, Handbuch der Organischen Chemie, Thieme Verlag, 1952, Vol. VIII, pages 120 et seq; by W. Siefken in Liebigs Annalen der Chemie, 562, 75 et seq (1949), by J. H. Saunders and J. R. Slocombe in Chem. Rev. 43, 203 (1948) and by A. A. Blagonravova and G. A. Levkovic in Uspechi Chim. 24, 93-119 (1955). The phosgenation reaction of the present invention may be carried out by the one-stage process, by the two-stage process (cold/hot phosgenation), by direct phosgenation of the polyamines, by phosgenation of the phosgenatable salts of the polyamines (particularly their hydrochlorides) and by phosgenation of the carbon dioxide adducts of the polyamines (carbamate method). The addition of the alcoholic component essential to the present invention may be made at the beginning of the phosgenation reaction where mixtures of amines and alcohols are used. The alcoholic component may also be added after the optional modification of the amines to be phosgenated (for example with hydrochloride or carbon dioxide). Where phosgenation is carried out in two stages, the alcoholic component may even be added after the cold phosgenation step in which the free amino groups are converted into hydrochloride and carbamoyl chloride groups. In the phosgenation of aromatic amines, it is best to use the two-stage process (cold/hot phosgenation of the free amines) whereas, in the phosgenation of aliphatic or cycloaliphatic polyamines, it is preferred to use the carbamate process.

The phosgenation reaction of the present invention is generally carried out at temperatures in the range from $-20°$ to $+200°$ C. using a suitable inert solvent. Examples of such inert solvents are chloroform, dioxane, dichloroethane, phosphorus oxychloride and, more particularly chlorobenzene or dichlorobenzene. Auxiliary solvents such as these need not be used in cases where relatively high molecular weight alcohols having a low hydroxyl number are used because these alcohols may also perform the function of a solvent.

In carrying out the phosgenation reaction of the present invention, it is important in principle to select reaction conditions such that there is no significant formation of carbonates (reaction of hydroxyl groups with phosgene via the intermediate stage of chlorocarbonic acid ester group), nor any significant formation of ureas (reaction of carbamoyl groups with free amino groups). The first of these two secondary reactions (i.e. formation of carbonates) only takes place to any significant extent at comparatively high temperatures. To avoid this secondary reaction, it is sufficient to keep the reaction mixture of (i) the alcoholic component, (ii) the amine optionally present in the form of phosgenatable salts, carbamates or hydrochloride/carbamoyl chloride (formed from amine and phosgene in the cold) and (iii) phosgene at temperatures below 100° C. (preferably at temperatures below 60° C.) until the urethane-forming reaction taking place between carbamoyl chloride groups and hydroxyl groups is complete. The formation of carbonates may also be suppressed by avoiding too large an excess of phosgene in the initial phase of the phosgenation reaction. However, precautionary measures such as these are largely unnecessary in cases where controlled extension of the alcohols used through carbonate bridges is desired. However, it is generally not desired to extend the hydroxyl component in this way.

The formation of ureas in the phosgenation process of the present invention may generally be avoided by ensuring that free amino groups and carbamoyl chloride groups are not simultaneously present. This may be accomplished where free amines are used as starting material, by immediately combining the starting amine with a quantity of phosgene such that there is at least 0.5 mole of phosgene for every mole of primary amino groups present.

The process of the present invention may be carried out, for example, by incorporating phosgene into a suitable solvent (e.g., by condensation at about $-20°$ C. to $+10°$ C.). In this way, solutions are prepared which contain, for example, from 10 to 200 (preferably from 35 to 120) parts by weight of phosgene to 100 parts by weight of solvent. The phosgene-containing solution may then be combined with the amine optionally present in the form of carbamate or phosgenatable salt (hydrochloride) and the alcoholic component at about $-20°$ to 40° C. (preferably at 0° to 25° C.).

The reaction mixture thus obtained is then advantageously kept at about 0° to 40° C. until the reactions taking place at that temperature are over. Thereafter the reaction mixture is heated to 50°–200° C. (preferably to 80°–180° C.), preferably in the presence of an excess of phosgene (more than 1 mole of phosgene per mole of primary amino groups present in the starting amine), to complete the phosgenation reaction. The excess of phosgene required may be provided by the continuous introduction of phosgene.

In cases where phosgenatable salts of the amines to be phosgenated (i.e. the corresponding hydrochlorides) or carbon dioxide adducts of the amines to be phosgenated (carbamate method) are used, these starting materials and also the alcoholic component may be present in the form of a solution or suspension in the solvent in which the phosgene is incorporated by condensation during the condensation process.

In another embodiment of the process of the present invention, the amine to be phosgenated is converted into the corresponding hydrochlorides/carbamoyl chlorides at $-20°$ to $+40°$ C. (preferably at 0° to 25° C.) in the absence of the alcoholic component which is only added to the reaction mixture after this cold phosgenation step has been completed.

On completion of the phosgenation reaction (when the evolution of hydrogen chloride stops), the phosgene present in the reaction mixture is removed, preferably by injecting an inert gas (such as dry nitrogen) into the hot or warm (for example 50° to 100° C.) reaction mixture and/or by applying a vacuum of for example 20 mbars. The reaction mixture is filtered in the presence or absence of a vacuum before or preferably after removal of the phosgene.

Solutions of NCO-prepolymers or NCO-semi-prepolymers in the solvent used for phosgenation are thus formed. Where an equivalent ratio between amino groups of the amine to be phosgenated and hydroxyl groups of the alcohol component of less than 1:0.5 is used, substantially monomer-free NCO-prepolymers may be obtained without thin-layer distillation. The products thus-obtained may be further processed in the usual way either in the form of a solution in the solvent used for phosgenation or after they have been freed from the solvent by distillation.

The described products obtained by the process of the present invention are polyisocyanates containing urethane groups which generally contain less than 2.0 wt. % of carbonate groups —O—CO—O— and less than 1.0 wt. % of urea groups —NH—CO—NH—. The isocyanate group (—NCO) and urethane group (—O—CO—NH—) contents of the products obtained by the process of the present invention may vary within wide limits depending upon the type of and quantitative ratio between the starting materials used. In general, the NCO-content amounts to between about 0.5 and 35 wt. % (preferably between 1 and 25 wt. %) while the urethane content amounts to between 0.5 and 20 wt. % (preferably between 1 and 4.0 wt. %).

A significant improvement in the production of distillable polyisocyanates is made possible by the use of monohydric and/or polyhydric alcohols in far less than stoichiometric quantities. Where the process of the present invention is carried out using alcohols such as these. organic diamines, (such as hexamethylene diamine) or diaminotoluenes are generally used as the amine component so that distillable diisocyanates are formed. The monohydric and/or polyhydric alcohols are preferably used in a quantity corresponding to an equivalent ratio of primary amino groups to hydroxyl groups of from 1:0.005 to 1:0.2. The alcohol(s) is/are preferably used in a quantity sufficient to liquefy the otherwise solid or resinous distillation residue. The optimal quantity and also the type of alcohol preferably used may readily be determined by a few simple tests. It is possible to use both individual alcohols and also mixtures of alcohols of the type mentioned above.

During working up of the phosgenation products by distillation, the urethane-group-containing derivatives formed from the alcohols remain in the distillation residue and improve its rheological behavior so that the distillation residues may be removed more easily from the distillation apparatus.

As already mentioned, the NCO-prepolymers or NCO-semiprepolymers obtainable by the process of the present invention preferably using at least dihydric alcohols may be used in accordance with techniques known to those in the art for the application for which products such as these are normally intended, particularly for the production of polyurethane plastics.

The products obtainable by the process of the present invention may also be used for the production of the corresponding polyamines (particularly polyaminopolyethers and/or polyesters). When used in accordance with the invention for this purpose, it is possible to convert the polyisocyanates of the present invention into the corresponding amines by hydrolytic conversion of the NCO-groups in accordance with the teachings of German Offenlegungsschriften 29 48 419; 30 39 600; 31 29 979; 31 31 252; 32 23 395; 32 23 400; 32 23 398; 32 23 397; 32 27 219 and 32 44 912.

In the following Examples, all the percentages quoted represent percentages by weight.

EXAMPLES

EXAMPLE 1 (Production of a Semiprepolymer)

600 g of gaseous phosgene (6.06 moles) were dissolved in 1.5 liter of o-dichlorobenzene by introduction at around 0° C. A solution heated to 60° C. of 150 g of 4,4'-diaminodiphenylmethane (0.76 mole) and 28.8 g of tripropylene glycol (0.15 mole) in 750 ml of o-dichlorobenzene was added at a temperature in the range from 0° to 8° C. The reaction mixture was heated slowly to 130° C. and, at the same time, a gentle stream of phosgene was introduced into the reaction vessel. Beyond 80° C., the solution began to clear with vigorous evolution of hydrogen chloride. After 105 minutes, the reaction was over and the reaction phase was almost completely clear. At an internal temperature of approximately 100° C., excess phosgene was driven out by a stream of nitrogen. The o-dichlorobenzene was distilled off at 20 mbar and the residue was filtered off hot from a few flakes of undissolved material. Final traces of volatile material were removed at 0.1 mbar/100° C. The yield was quantitative. For further data, see Table 1.

EXAMPLE 2

400 g of gaseous phosgene (4.04 moles) were dissolved in 700 ml of chlorobenzene by introduction at around 0° C. A solution of 61 g of 2,4-diaminotoluene (0.5 mole) and 500 g of a polypropylene glycol having an OH-number of 56 (0.25 mole) in 400 ml of chlorobenzene was added over a period of 20 minutes to the solution cooled with a cooling mixture of ice and sodium chloride. The reaction mixture was then heated to reflux temperature over a period of 150 minutes during which a gentle stream of phosgene was introduced into the reaction vessel. Vigorous evolution of gas began at 50° C., the reaction mixture cleared at the same time. By applying a water jet pump vacuum, the chlorobenzene was distilled off. Minor undissolved residues were filtered off and volatile constituents were removed at 100° C./0.1 mbar. The yield amounted to 99%. For further data, see Table 1.

EXAMPLE 3

400 g of gaseous phosgene (4.04 moles) were dissolved in 500 ml of chlorobenzene by introduction at around 0° C. A suspension heated to 50° C. of 54 g of p-phenylene diamine (0.5 mole) in a mixture of 250 g of a polypropylene glycol (OH number 112) and 500 ml of chlorobenzene was then added over a period of 15 minutes at an internal temperature in the range from 0° to 12° C. The reaction mixture was heated to reflux temperature (126° C.) over a period of 30 minutes and kept at that temperature for 150 minutes. Vigorous evolution of hydrogen chloride began when the internal temperature reached 50° C. During the evolution of hydrogen chloride, a gentle stream of phosgene was continuously introduced into the reaction vessel. When the evolution of gas stopped, most of the chlorobenzene was distilled off by applying a vacuum of 20 mbar. Minor residues of insoluble accompanying products were filtered off under suction and the NCO-prepolymer was freed from volatile substances at 100° C./0.1 mbar. The yield was quantitative. For further data, see Table 1.

EXAMPLE 4

34.8 g (0.3 mole) of hexamethylene diamine were dissolved in 300 ml of o-dichlorobenzene. This solution was saturated by the introduction of carbon dioxide $CO_2$ at 90° to 95° C. 480 g of a trifunctional polyether (OH number 35) formed by the blockwise addition of propylene oxide and then ethylene oxide on trimethylol propane containing at least 95% of primary OH-groups were added to the carbamate suspension formed and the resulting mixture cooled to 0° C. At that temperature, 70 g of phosgene were incorporated by condensation, accompanied by the evolution of carbon dioxide. After the evolution of carbon dioxide had stopped, the reaction mixture was heated to 160° C. and, at the same time, a gentle stream of phosgene was introduced into the reaction vessel. After a reaction time of 8 hours, the solution was clear. At an internal temperature falling from 160° to 120° C., excess phosgene was driven out over a period of 30 minutes by a stream of nitrogen.

The solvent was distilled off at 130° C./20 mbar and then at 120° C./0.1 mbar, after which traces of insoluble product were filtered off under suction. The yield was quantitative. For further data, see Table 1.

TABLE 1

|  | Example 1 | Example 2 | Example 3 | Example 4 |
|---|---|---|---|---|
| NH$_2$:OH equivalent ratio | 5.05 | 2 | 2 | 2 |
| NCO—value (%)[1] | 23.6 | 3.7 | 6.8 | 2.4 |
| NCO—value (%)[2] | 23.3 | 3.6 | 6.62 | 2.4 |
| Carbonate[3] | — | — | traces | traces |
| Hydrolyzable Cl (%)[4] | 0.17 | 0.05 | 0.05 | 0.11 |
| Viscosity (mPas)[5] | 750 | 2100 | 6050 | 12100 |
| Monomer content (%)[6] | 70 | 1.3 | 2.1 | 0.6 |

[1] Observed
[2] Calculated
[3] According to IR as a band at 1780 cm$^{-1}$
[4] After boiling with methanolic KOH, Mohr's method
[5] as measured by a rotary viscosimeter at 24° C.
[6] As measured by gas chromatography

EXAMPLE 5

400 g of gaseous phosgene were condensed in 700 ml of chlorobenzene by introduction at 0° to −10° C. A solution of 61 g (0.5 mole) of 2,4-diaminotoluene, 100 g of the polypropylene glycol of Example 2 (0.05 mole) and 400 ml of chlorobenzene was added dropwise over a period of 30 minutes at an internal temperature of 5° to 18° C. The reaction mixture was then heated for 2 hours to 125° C. and, at the same time, a gentle stream of phosgene was introduced into the reaction vessel. After the evolution of hydrogen chloride, which began beyond 50° C. had stopped, excess phosgene was driven out by a stream of nitrogen. The chlorobenzene was distilled off in vacuo. 60 g of pure 2,4-tolylene diisocyanate were distilled off from the residue by applying an oil pump vacuum (92°-95° C./0.2 mbar). At 0.2 mbar pressure and at a bath temperature of 200° C., no more 2,4-diisocyanatotoluene distilled over. The residue was made up of 99 g of a liquid having an NCO-content of 4.3%, a viscosity at 23° C. of 3500 mPa.s and a free tolylene diisocyanate content, as determined by gas chromatography, of 1.4%.

EXAMPLE 6

50 g (0.505 mole) of phosgene were condensed in 700 ml of chlorobenzene at 0° to −10° C. A solution heated to 60° C. of 61 g (0.5 mole) of 2,4-diaminotoluene in 500 ml of chlorobenzene was added dropwise with vigorous stirring over a period of 20 minutes at an internal temperature rising from −5° to 19° C. After stirring for another 15 minutes at 20° C., a white heterogeneous reaction mixture was obtained. 500 g (0.25 mole) of the polypropylene glycol of Example 2 were then added with stirring at 20° C., followed by heating to an internal temperature of 120° C. After 90 minutes, the reaction mixture was yellow in color and was then heated for another 3 hours, during which there was a moderate evolution of gas. Residual gas was removed from the reaction mixture by a stream of nitrogen. The progress of the reaction was followed by IR-spectroscopy on the basis of the increase in intensity of the urethane band at 1722 cm$^{-1}$ and the reduction in intensity of a band associated with the

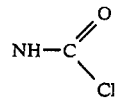

-group at 1775 cm$^{-1}$. Thereafter the reaction mixture was cooled again and another 350 g (3.54 moles) of phosgene were incorporated by condensation at −5° to 0° C. On heating to 125° C., there was an evolution of gas beyond 60° C. At the same time, a gentle stream of phosgene was introduced into the reaction vessel. Dissolution occurred towards the end of the reaction. Excess phosgene and solvent were removed in the same way as in Example 5. 551 g of a slightly clouded, brown liquid having a viscosity of 6500 mPa.s/23° C. and an NCO-content of 3.8% were obtained.

EXAMPLE 7 (Application Example)

A mixture of 6.1 g (0.15 mole) of sodium hydroxide, 50 ml of water and 60 ml of acetone was initially introduced into the reaction vessel. 99 g of the NCO-prepolymer of Example 5 having an NCO-content of 4.3% (0.1 mole) were then added over a period of 10 minutes with intensive stirring and cooling with an ice bath so that the internal temperature did not rise above 25° C. On completion of the addition, the mixture was stirred for 15 minutes at 20° C. and then heated for 1 hour to 80° C. On cooling, the reaction mixture separated into two phases. The lower phase contained most of the salt and was discarded. The upper phase was separated off, water and acetone were distilled off at 100° C./20-1 mbar and the dark brown residue was filtered. The residue was an oligomeric polyamine having a viscosity at 25° C. of 9900 mPa.s, an NH-number of 39.6 (mg of KOH/g) and a primary amine nitrogen content of 0.99%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of polyisocyanates comprising phosgenating a primary polyamine in the presence of a compound containing at least one primary and/or secondary alcoholic hydroxyl group selected from the group consisting of:
   (a) alkane polyols free from ether and ester groups having a molecular weight of from 62 to 250,
   (b) cycloalkane polyols free from ether and ester groups having a molecular weight of from 116 to 250,
   (c) polyols containing ether groups having a molecular weight of from 106 to 10,000 provided that when the polyamine is an aromatic polyamine the polyol containing ether groups is a polypropylene glycol and
   (d) mixtures thereof,
in a manner such that an equivalent ratio of primary amino groups to hydroxyl groups of from 1:0.005 to 1:0.99 is maintained during the phosgenation.

2. The process of claim 1 in which the primary polyamine is converted into a phosgenatable salt or a carbon dioxide adduct before phosgenation.

3. The process of claim 2 in which the phosgenation is carried out in two stages.

4. The process of claim 3 in which the compound containing alcoholic hydroxyl groups is present only in the second stage.

5. The process of claim 4 in which the equivalent ratio of primary amino groups to hydroxyl groups during the second stage is maintained at from 1:0.005 to 1:0.2.

6. The process of claim 5 in which any excess monomeric polyisocyanate is distilled off after phosgenation.

7. The process of claim 1 in which the phosgenation is carried out in two stages.

8. The process of claim 7 in which the compound containing alcoholic hydroxyl groups is present only in the second stage.

9. The process of claim 7 in which the equivalent ratio of primary amino groups to hydroxyl groups during the second stage is maintained at from 1:0.005 to 1:0.2.

10. The process of claim 9 in which any excess monomeric polyisocyanate is distilled off after phosgenation.

11. The process of claim 1 in which the primary polyamine is a diprimary diamine having a molecular weight in the range of from 60 to 500.

12. The process of claim 1 in which the compound containing alcoholic hydroxyl groups is a polyol or mixture of polyols having an average hydroxyl functionality of from 2 to 3.

13. The process of claim 12 in which the primary polyamine is a diprimary aromatic diamine having a molecular weight of from 108 to 250.

14. The process of claim 1 in which the primary polyamine is a diprimary aromatic diamine having a molecular weight of from 108 to 250.

15. A polyisocyanate produced by phosgenating a primary polyamine in the presence of at least one compound containing a primary and/or secondary alcoholic hydroxyl group in a manner such that an equivalent ratio of primary amino groups to hydroxyl groups of from 1:0.005 to 1:0.99 is maintained during the phosgenation.

16. The polyisocyanate of claim 15 in which the primary polyamine has been converted to a phosgenatable salt or a carbon dioxide adduct before phosgenation.

17. The polyisocyanate of claim 15 in which the primary polyamine is a diprimary diamine having a molecular weight in the range of from 60 to 500.

18. The polyisocyanate of claim 15 in which the compound containing alcoholic hydroxyl groups is a polyol or mixture of polyols having an average hydroxyl functionality of from 2 to 3.

19. A process for the production of polyurethanes comprising:
   (a) phosgenating a primary polyamine in the presence of at least one compound containing a primary and/or secondary alcoholic hydroxyl group in a manner such that an equivalent ratio of primary amino groups to hydroxyl groups of from 1:0.005 to 1:0.99 is maintained during the phosgenation and
   (b) reacting the phosgenation product of (a) with a compound containing isocyanate-reactive groups.

20. A process for the production of polyamines comprising:
   (a) phosgenating a primary polyamine in the presence of at least one compound containing a primary and/or secondary alcoholic hydroxyl group in a manner such that an equivalent ratio of primary amino groups to hydroxyl groups of from 1:0.005 to 1:0.99 is maintained during the phosgenation to produce a polyisocyanate and
   (b) hydrolytically converting the isocyanate groups in the polyisocyanate formed in (a) into amino groups.

* * * * *